United States Patent
Zhang et al.

(10) Patent No.: US 7,555,351 B2
(45) Date of Patent: Jun. 30, 2009

(54) PULMONARY ARTERY LEAD FOR ATRIAL THERAPY AND ATRIAL PACING AND SENSING

(75) Inventors: Yongxing Zhang, Little Canada, MN (US); Christopher P. Knapp, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 704 days.

(21) Appl. No.: 10/895,748

(22) Filed: Jul. 21, 2004

(65) Prior Publication Data
US 2004/0260375 A1    Dec. 23, 2004

Related U.S. Application Data

(63) Continuation-in-part of application No. 10/325,659, filed on Dec. 19, 2002.

(51) Int. Cl.
*A61N 1/05* (2006.01)
(52) U.S. Cl. .................................. 607/126; 607/116
(58) Field of Classification Search .................. 607/5, 607/115, 116, 119, 120–123, 126, 130
See application file for complete search history.

(56) References Cited

U.S. PATENT DOCUMENTS

| | | | |
|---|---|---|---|
| 3,995,623 A * | 12/1976 | Blake et al. | 600/381 |
| 4,402,328 A | 9/1983 | Doring | |
| 4,488,561 A | 12/1984 | Doring | |
| 4,595,009 A | 6/1986 | Leinders | |
| 4,627,439 A | 12/1986 | Harris | |
| 4,641,656 A | 2/1987 | Smits | |
| 4,643,201 A | 2/1987 | Stokes | |
| 4,759,378 A | 7/1988 | Swendson et al. | |
| 4,986,270 A | 1/1991 | Cohen | |
| 5,000,190 A | 3/1991 | Petre | |
| 5,029,585 A | 7/1991 | Lieber et al. | |
| 5,144,960 A | 9/1992 | Mehra et al. | |
| 5,314,462 A | 5/1994 | Heil et al. | |
| 5,387,233 A | 2/1995 | Alferness et al. | |
| 5,403,351 A | 4/1995 | Saksena | |
| 5,405,374 A | 4/1995 | Stein | |
| 5,411,527 A | 5/1995 | Alt | |
| 5,423,772 A | 6/1995 | Lurie et al. | |
| 5,423,865 A | 6/1995 | Bowald et al. | |
| 5,433,729 A | 7/1995 | Adams et al. | |

(Continued)

OTHER PUBLICATIONS

Barin, E. S., et al., "The right ventricular outflow tract as an alternative permanent pacing site: long-term follow-up", *Pacing and Clinical Electrophysiology*, 14(I), (1991),3-6.

(Continued)

*Primary Examiner*—Carl H Layno
*Assistant Examiner*—Brian T Gedeon
(74) *Attorney, Agent, or Firm*—Schwegman, Lundberg & Woessner, P.A.

(57) ABSTRACT

A lead includes a lead body extending from a proximal end to a distal end and having an intermediate portion. A shocking electrode is disposed proximate the distal end of the lead body, and a pacing electrode is disposed along the intermediate portion of the lead body. The distal end of the lead body includes a pre-formed biased shape.

23 Claims, 8 Drawing Sheets

U.S. PATENT DOCUMENTS

| | | | |
|---|---|---|---|
| 5,433,742 A | | 7/1995 | Willis |
| 5,476,499 A | * | 12/1995 | Hirschberg ................. 607/123 |
| 5,571,159 A | | 11/1996 | Alt |
| 5,609,621 A | | 3/1997 | Bonner |
| 5,628,779 A | | 5/1997 | Bornzin et al. |
| 5,643,338 A | * | 7/1997 | Bornzin et al. .............. 607/123 |
| 5,697,965 A | * | 12/1997 | Griffin, III .................. 607/123 |
| 5,788,647 A | | 8/1998 | Eggers |
| 5,800,498 A | | 9/1998 | Obino et al. |
| 5,861,023 A | | 1/1999 | Vachon |
| 5,922,014 A | | 7/1999 | Warman et al. |
| 5,925,073 A | * | 7/1999 | Chastain et al. ............. 607/122 |
| 6,006,122 A | | 12/1999 | Smits |
| 6,021,354 A | | 2/2000 | Warman et al. |
| 6,076,014 A | | 6/2000 | Alt |
| 6,093,982 A | | 7/2000 | Kroll |
| 6,117,128 A | | 9/2000 | Gregory |
| 6,122,553 A | | 9/2000 | Idekar et al. |
| 6,132,390 A | | 10/2000 | Cookston et al. |
| 6,245,064 B1 | | 6/2001 | Lesh et al. |
| 6,363,286 B1 | | 3/2002 | Zhu et al. |
| 6,363,287 B1 | | 3/2002 | Brabee et al. |
| 6,501,992 B1 | | 12/2002 | Belden et al. |
| 6,532,378 B2 | * | 3/2003 | Saksena et al. ............. 600/381 |
| 6,718,211 B2 | | 4/2004 | Smits |
| 6,760,619 B1 | | 7/2004 | Helland et al. |
| 6,882,886 B1 | * | 4/2005 | Witte et al. ................. 607/122 |
| 2001/0031987 A1 | | 10/2001 | Saksena et al. |
| 2002/0065544 A1 | | 5/2002 | Smits |
| 2004/0122496 A1 | | 6/2004 | Zhang et al. |
| 2004/0122497 A1 | | 6/2004 | Zhang et al. |
| 2004/0122498 A1 | | 6/2004 | Zhang et al. |
| 2004/0260374 A1 | | 12/2004 | Zhang et al. |

OTHER PUBLICATIONS

Belham, M , et al., "Pacing Different ventricular site with active and passive fixation leads: comparison of pacing energy requirements", *Pacing and Clinical Electrophysiology*, 21(II), (1999),977.

Buckingham, T. A., et al., "Right ventricular outflow tract pacing", *Pacing and Electrophysiology*, 20(5 Pt 1), (1997), 1237-42.

Giudici, M. , "Comparison of right ventricular outflow tract and apical lead permanent pacing on cardiac output", *American Journal of Cardiology*, 79(2), (1997),209-212.

Giudici, M C., "Improvement in Cardiac Output with Right Ventricular Outflow Septal Pacing Compare to Apical Pacing is Independent of Pre-existing Conduction Disease", *Pacing and clinical electrophysiology : PACE*, 23(4), (2000),748.

Giudici, M. C., et al., "Right ventricular outflow tract pacing improves haemodynamics in patients with class III-IV heart failure and existing apical leads", *Pacing and Electrophysiology*, 21(II) Abstract 751, (1998),2 pgs.

Harris, Z I., et al., "Changes in left ventricular function and dimensions between apical and septal lead position with dual chamber pacing in normally functioning hearts", *Pacing and Clinical Electrophysiology*, 22(II) Abstract, (1999),751.

Harris, Z. I., et al., "Septal/right ventricular outflow tract (RVOT) lead placement", *Pacing and Electrophysiology*, 22(12), (1999),1854-1855.

Hirschberg, J. , "A New Dual Chamber Single Lead System", *Pacing & Electrophysiology*, 17(11 Pt 2), (Nov. 1994),1870-1872.

Libbus, Imad , "Lead for Stimulating the Baroreceptors in the Pulmonary Artery", U.S. Appl. No. 10/746,861, Filed Dec. 24, 2003, 21 pgs.

Lubinski, A. , et al., "Implantation and follow-up of ICD leads implanted in the right ventricular outflow tract", *Pacing and Electrophysiology*, 23(11 Pt 2), (2000),1996-98.

Mera, F. , et al., "A comparison of ventricular function during high right ventricular septal and apical pacing after his-bundle ablation for refractory atrial fibrillation", *Pacing and Clinical Electrophysiology*, 22(8), (1999),1234-39.

Rosenqvist, M , "The effect of ventricular activation sequence on cardiac performance during pacing", *Pacing and Electrophysiology*, 19(9), (1996),1279-1286.

Scheiner, Avram , "Stimulation Lead for Stimulating the Baroreceptors in the Pulmonary Artery", U.S. Appl. No. 10/746,852, filed Dec. 24, 2003, 25 pgs.

Schwaab, B , et al., "Influence of right ventricular stimulation site on left ventricular function in atrial synchronous ventricular pacing", *Journal of the American College of Cardiology*, 33(2), (1999),317-23.

Schwaab, B , et al., "Surface ECG guided right ventricular septal lead implantation for the reduction of paced QRS duration", *Pacing and Clinical Electrophysiology*, 22(II), (1999),806.

Staniewicz, J , et al., "Short versus long term results in right ventricular outflow tract pacing- prospective randomized study", *Pacing and Electrophysiology*, 21(II) Abstract 419, (1998),2 pgs.

Tang, A.S.L. , et al., "Nonthorocotomy implantation of cardioverter defibrillators; preliminary experience with a defibrillation lead paced at the right ventricular outflow tract", *Pacing and Electrophysiology*, 19(6), (1996),960-964.

Tantengco, M. V., et al., "Left ventricular dysfunction after long-term right ventricular apical pacing in the young", *American Journal of Cardiology*, 37(8), (Jun. 15, 2001),2093-100.

Tse, Hung-Fat , "Functional abnormalities in patients with permanent right ventricular pacing—The effect of sites of electrical stimulation", *Journal of the American College of Cardiology*, 40(8), (Oct. 16, 2002),1451-1458.

Victor, F. , et al., "Optimal right ventricular pacing site in chronically implanted patients", *Journal of the American College of Cardiology*, 33(2), (1999),311-6.

Vlay, S. C., et al., "Alternative locations for internal defibrillator electrodes", *Pacing and Clinical Electrophysiology*, 21(6), (1998),1309-12.

Wolfhard, U. F., et al., "Alternative lead positioning in the right ventricular outflow tract in transvenous implantation of ICDs", *Pacing and Electrophysiology*, 18(1 Pt 2), (1995),179-81.

Zhang, Yongxing , "Delivery System and Method for Pulmonary Artery Leads", U.S. Appl. No. 10/970,265, filed Oct. 20, 2004, 21 pgs.

Scherlag, B. J., et al., "Endovascular stimulation within the left pulmonary artery to induce slowing of heart rate and paroxysmal atrial fibrillation.", *Cardiovasc Research*, 54(2), (May 2002),470-475.

U.S. Appl. No. 10/325,433 Non Final office action mailed Jun. 1, 2007, 9 pgs.

U.S. Appl. No. 10/325,433 Non-Final Office Action mailed Nov. 16, 2005, 14 pgs.

U.S. Appl. No. 10/325,433 Non-Final Office Action mailed Jul. 31, 2006, 15 pgs.

U.S. Appl. No. 10/325,433 Response filed Nov. 22, 2006 to Non final office action mailed Jul. 31, 2006, 17 pgs.

U.S. Appl. No. 10/325,433 Response filed May 16, 2006 to Non final office action mailed Nov. 16, 2005, 16 pgs.

U.S. Appl. No. 10/325,433, Response filed Sep. 4, 2007 to Non-Final Office Action mailed Jun. 1, 2007, 15 pgs.

U.S. Appl. No. 10/325,658 Advisory Action mailed Mar. 8, 2007, 3 pgs.

U.S. Appl. No. 10/325,658 Advisory Action mailed Apr. 3, 2007, 3 pgs.

U.S. Appl. No. 10/325,658 Final office action mailed Dec. 22, 2006, 10 pgs.

U.S. Appl. No. 10/325,658 Non Final office action mailed Jul. 7, 2006, 13 pgs.

U.S. Appl. No. 10/325,658 Non Final office action mailed Nov. 22, 2005, 20 pgs.

U.S. Appl. No. 10/325,658 Non Final Office Action mailed Aug. 23, 2007, 11 pgs.

U.S. Appl. No. 10/325,658 Response filed Feb. 22, 2007 to Final office action mailed Dec. 22, 2006, 23 pgs.

U.S. Appl. No. 10/325,658 Response filed Apr. 23, 2007 to Advisory Action mailed Apr. 3, 2007, 8 pgs.

U.S. Appl. No. 10/325,658 Response filed May 18, 2006 to Non Final office action mailed Nov. 22, 2005, 24 pgs.

U.S. Appl. No. 10/325,658 Response filed Oct. 10, 2006 to Non Final office action mailed Jul. 7, 2006, 20 pgs.

U.S. Appl. No. 10/325,659 Non Final Office Action mailed Jun. 1, 2007, 9 pgs.

"U.S. Appl. No. 10/325,433 Notice of Allowance mailed May 3, 2007", 9 pgs.

"U.S. Appl. No. 10/325,659 Advisory Action mailed Jul. 23, 2007", 3 pgs.

"U.S. Appl. No. 10/325,659 Final Office Action mailed May 3, 2007", 17 pgs.

"U.S. Appl. No. 10/325,659 Non-Final Office Action mailed Jan. 25, 2006", 14 pgs.

"U.S. Appl. No. 10/325,659 Non-Final Office Action mailed Aug. 4, 2006", 14 pgs.

"U.S. Appl. No. 10/325,659 Non-Final Office Action mailed Aug. 9, 2005", 16 pgs.

"U.S. Appl. No. 10/325,659 Response filed Dec. 9, 2005 to Non Final Office Action mailed Aug. 9, 2005", 15 pgs.

"U.S. Appl. No. 10/325,659 Response filed May 25, 2006 to Non final office action mailed Jan. 25, 2006", 14 pgs.

"U.S. Appl. No. 10/325,659 Response filed Jul. 3, 2007 to Final office action mailed May 3, 2007", 15 pgs.

"U.S. Appl. No. 10/325,659 Response filed Feb. 5, 2007 to Non final office action mailed Aug. 4, 2007", 13 pgs.

"U.S. Appl. No. 10/895,747 Advisory Action mailed Mar. 20, 2007", 3 pgs.

"U.S. Appl. No. 10/895,747 Amendment and Response mailed Oct. 18, 2006", 14 pgs.

"U.S. Appl. No. 10/895,747 Amendment and Response to Final Office Action mailed Feb. 22, 2007", 18 pgs.

"U.S. Appl. No. 10/895,747 Final Office Action mailed Dec. 22, 2006", 9 pgs.

"U.S. Appl. No. 10/895,747 Non Final office action mailed Jul. 5, 2007", 13 pgs.

"U.S. Appl. No. 10/895,747 Non-Final Office Action mailed Jul. 18, 2006", 16 pgs.

"U.S. Appl. No. 10/895,747 Request for Continued Examination mailed Apr. 23, 2007", 1 pg.

* cited by examiner

PULMONARY ARTERY LEAD FOR ATRIAL THERAPY AND ATRIAL PACING AND SENSING

RELATED APPLICATION

This application is a continuation-in-part and claims priority of invention under 35 U.S.C. §120 from U.S. application Ser. No. 10/325,659, filed Dec. 19, 2002, which is incorporated herein by reference.

FIELD

This invention relates to the field of medical leads, and more specifically to an implantable lead.

BACKGROUND

Leads implanted in or about the heart have been used to reverse certain life threatening arrhythmia, or to stimulate contraction of the heart. Electrical energy is applied to the heart via the leads to return the heart to normal rhythm.

For example, one technique to apply therapy to the left atrium of the heart is to implant the electrode through the coronary sinus to reach a location below the left atrium. However, it can be difficult to locate the coronary sinus ostium, thus implantation time can be excessive, or the procedure can be unsuccessful. Also, some therapies require two or more electrodes located in separate chambers or locations within a heart. Typically, these electrodes are on different leads. However, implanting two or more leads within a heart increases the costs and difficulties of the procedure.

SUMMARY

A lead includes a lead body extending from a proximal end to a distal end and having an intermediate portion. A shocking electrode is disposed proximate the distal end of the lead body, and a pacing electrode is disposed along the intermediate portion of the lead body. The distal end of the lead body includes a pre-formed biased shape. In one option, the lead can include a second shocking electrode located proximally from the pacing electrode.

One aspect includes a lead body extending from a proximal end to a distal end and having an intermediate portion, the distal end adapted for being passively fixated within a pulmonary artery. The lead includes a shocking electrode disposed along the distal end of the lead body and a pacing electrode disposed along the intermediate portion of the lead body. The lead body is configured such that when the shocking electrode is within a pulmonary artery the pacing electrode is located within a right atrium or a superior vena cava.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
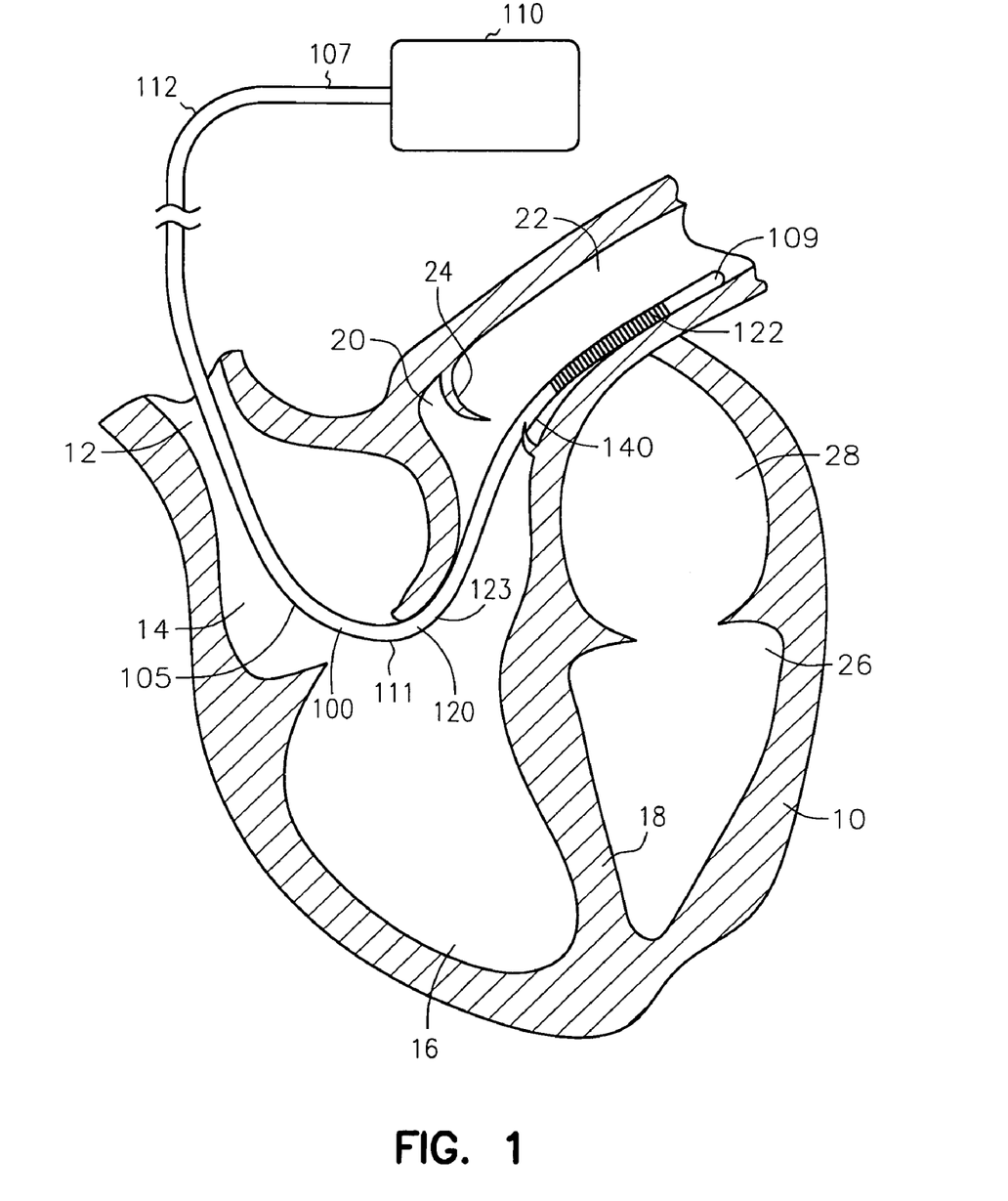
FIG. 1 shows a view of a lead, according to one embodiment, implanted within a heart.

FIG. 1 shows a view of a lead 100 implanted within a heart 10. Heart 10 generally includes a superior vena cava 12, a right atrium 14, a right ventricle 16, a left ventricle 26, a left atrium 28, a ventricular septum 18, and a ventricular outflow tract 20, which leads to a pulmonary artery 22, having a pulmonary artery valve 24. In one embodiment, lead 100 is adapted to deliver defibrillation pulses to heart 10 via an electrode 122. Lead 100 is part of an implantable system including a pulse generator 110, such as a defibrillator.

Pulse generator 110 can be implanted in a surgically-formed pocket in a patient's chest or other desired location. Pulse generator 110 generally includes electronic components to perform signal analysis and processing, and control. Pulse generator 110 can include a power supply such as a battery, a capacitor, and other components housed in a case. The device can include microprocessors to provide processing, evaluation, and to determine and deliver electrical shocks and pulses of different energy levels and timing for ventricular defibrillation, cardioversion, and pacing to heart 10 in response to cardiac arrhythmia including fibrillation, tachycardia, and bradycardia.

In one embodiment, lead 100 includes a lead body 105 extending from a proximal end 107 to a distal end 109 and having an intermediate portion 111. Lead 100 includes one or more conductors, such as coiled conductors, to conduct energy from pulse generator 110 to heart 10, and also to receive signals from the heart. The lead further includes outer insulation 112 to insulate the conductor. The conductors are coupled to one or more electrodes, such as electrode 122. Lead terminal pins are attached to pulse generator 110. The system can include a unipolar system with the case acting as an electrode or a bipolar system.

In one embodiment, electrode 122 includes a shock electrode adapted for delivering shock pulses to heart 10. For instance, lead 100 can be designed for placement of shock electrode 122 within the pulmonary artery 22 to deliver shock pulses to the left atrium 28. In one embodiment, lead 100 is adapted for pulmonary artery placement of shock electrode 122 while utilizing pulmonary artery 22 for lead fixation. For example, in one embodiment electrode 122 is disposed proximate distal end 109. Electrode 122 can include a shocking coil electrode designed to deliver energy pulses of approximately 0.1 to 60 Joules. One embodiment delivers defibrillation shocks of between approximately 3 Joules and approximately 60 Joules.

In one embodiment, lead body 105 includes a pre-formed, biased V-shape or J-shape 120 formed in the intermediate portion 111 of the lead body. J-shape 120 is located such that electrode 122 is located distally from a bottom 123 of the pre-formed J-shape 120. Pre-formed J-shape 120 can be in either 2D or 3D. J-shaped portion 120 of lead 100 allows for better placement of electrode 122 within the pulmonary artery. To pre-form the lead, the lead can be manufactured such that it is biased in the J-shape. Thus, the lead naturally reverts to the J-shape when it is implanted. For example, the lead body can be formed in the pre-biased shape or the conductor coils can be formed in the pre-biased shape to bias the lead body into the shape. When implanted, the bottom 123 of the J-shape 120 is within the right ventricle 16 and electrode 122 is positioned past the pulmonary valve 24 such that the electrode is within the pulmonary artery above the left atrium 28.

The pre-formed J-shaped lead design enhances the electrode stability and contact. This can help result in lower thresholds because of better electrode contacts. Moreover, it allows for easier implantation of the lead for delivering pulses to the left atrium. The present lead and method allow for utilization of the pulmonary artery to deliver the pulses to the left atrium. This allows for relatively easier implantation techniques.

In one embodiment, at least a portion of lead 100 can include an anti-thrombosis coating 140, such as Hypren™ or polyethleneglycol, for example. Coating 140 can be placed on the lead, for example on the coil electrode, on body 105, or on other segments of the lead.

In some embodiments, lead 100 can be configured to allow both a stylet or catheter delivery. For example, an opening can be left through the middle of the lead to allow a stylet to be used.

In one embodiment, distal end 109 is adapted for being passively fixated within a pulmonary artery. For example, as will be discussed below, a pre-formed biased distal portion 109 can be provided. In some embodiments, to be discussed below, an active fixation technique is utilized. Some embodiments utilize neither passive nor active fixation, relying on the J-shape 120 and gravity to hold the electrode 122 in place within the pulmonary artery.

Figure 2:
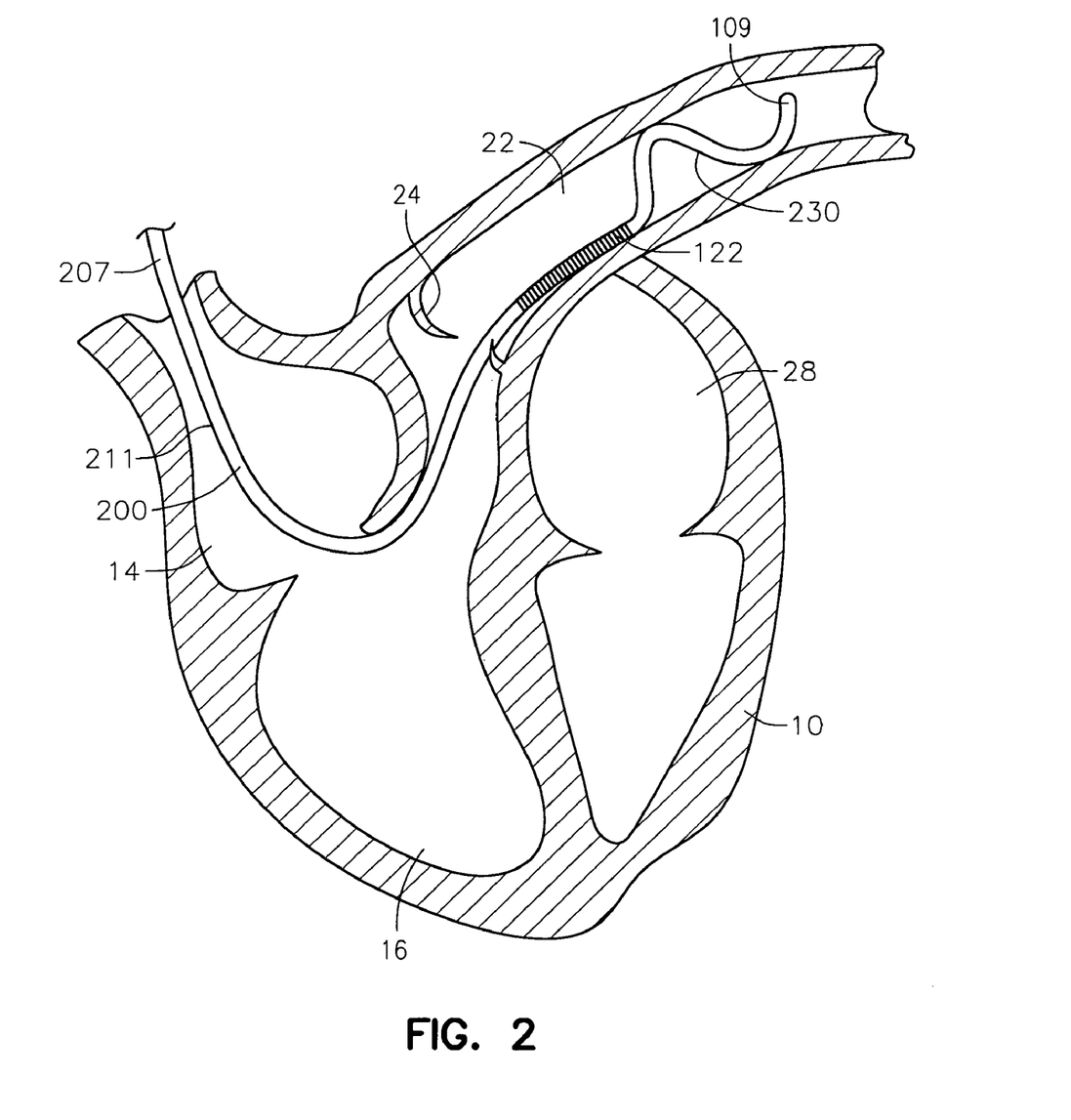
FIG. 2 shows a view of a lead, according to one embodiment, implanted within a heart.

FIG. 2 shows a front view of a lead 200 according to one embodiment, positioned within heart 10. Lead 200 includes some of the components discussed above for lead 100, and the above discussion is incorporated herein. Lead 200 extends from a proximal end 207 to a distal end 209 and includes an intermediate portion 211. Lead 200 can be implanted in heart 10 with distal end 209 located within the pulmonary artery and electrode 122 positioned within the pulmonary artery 22 past valve 24. Some embodiments utilize a branch of the pulmonary artery for fixation of distal end 209.

In one embodiment, lead 200 does not include the pre-formed, biased J-shaped portion 120 discussed above. Lead 200 includes a pre-formed, biased shape 230 on distal end 209 of lead 200. Pre-formed biased shape 230 can include a curved shape such as an S-shape, a C-shape, a J-shape, an O-shape, and other non-linear shapes adapted for contacting one or sides of the pulmonary artery (or a branch of the pulmonary artery) to provide sufficient fixation of the lead. The preformed shape 230 can be in 2-D or 3-D. Lead 200 is easier to implant and explant because of the passive fixation which is allowed by the biased shape of the distal portion of lead 200. For example, passive fixation allows for easier adjustment of electrode placement, and is easier to explant. Moreover, there is less trauma or perforation to endocardium tissue than with active fixation leads, which can yield lower pacing thresholds. Moreover, there is less trauma to the septal/outflow tract caused by active fixation at the septal/outflow tract location.

Figure 3:
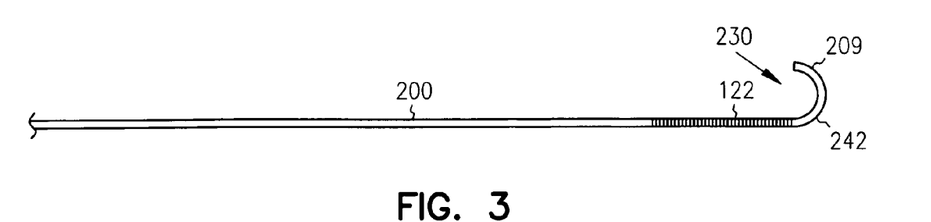
FIG. 3 shows a distal portion of a lead according to one embodiment.

Pre-formed, biased shape 230 can take various configurations. For example, FIG. 3 shows distal portion 209 of lead 200 according to one embodiment. In this example, pre-formed, biased shape 230 includes a J-shaped curve 242 at a distal tip of the lead body. J-shaped curve 242 can be positioned within pulmonary artery 22 or in one of the branch arteries off of the pulmonary artery to fixate the distal end of the lead within the pulmonary artery.

Figure 4A:
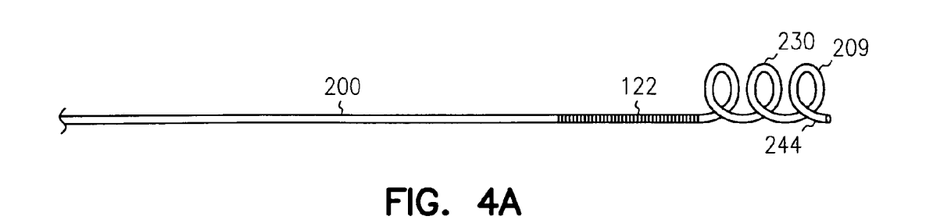
FIG. 4A shows a distal portion of a lead according to one embodiment.

FIG. 4A shows distal portion 209 of lead 200 according to one embodiment. In this example, pre-formed, biased shape 230 includes a spiral configuration 244. The pre-formed, biased shape generally can include at least two lead surfaces which are dimensioned and positionable such that the surfaces contact opposing walls of the pulmonary artery.

Figure 4B:
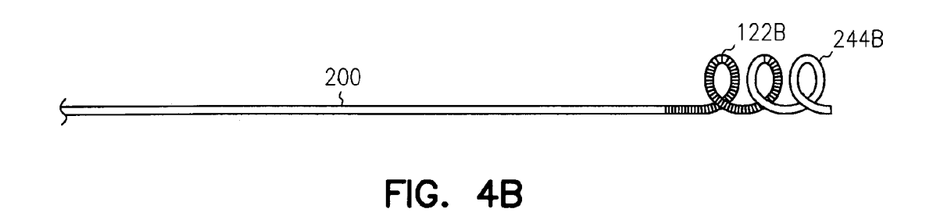
FIG. 4B shows a distal portion of a lead according to one embodiment.
Figure 4C:
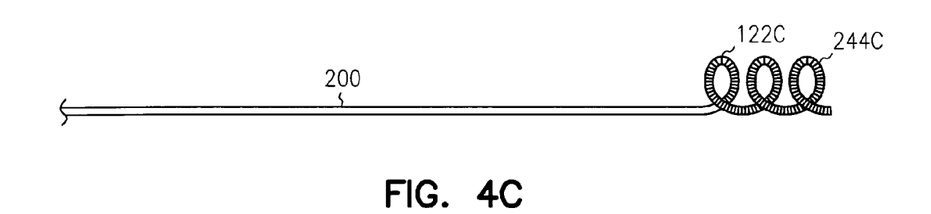
FIG. 4C shows a distal portion of a lead according to one embodiment.

The pre-formed biased shapes 230 discussed above and below can also be formed at least partly by the coil electrode itself. For example, FIG. 4B shows lead 200 having a spiral configuration 244B which partially includes a coil electrode 122B formed into a coil shape and at least partially defining spiral configuration 244B. FIG. 4C shows lead 200 having a spiral configuration 244C and a coil electrode 122C covers the distal end of the lead. In these examples of FIGS. 4B and 4C, the coil electrodes 122B and 122C can be pre-formed in the spiral shape to bias the distal end of the lead into the spiral configuration.

Figure 5:
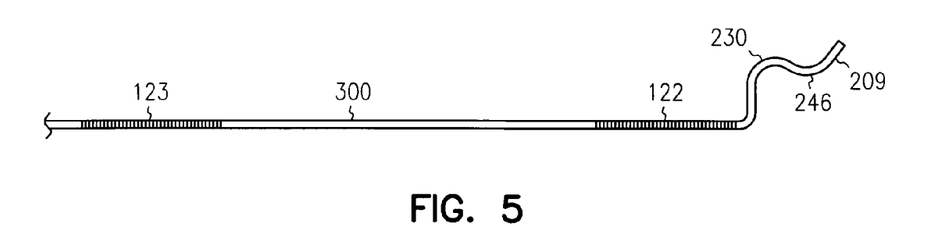
FIG. 5 shows a view of a lead, according to one embodiment.

FIG. 5 shows a lead 300 according to one embodiment. Lead 300 includes a second electrode 123, such as a coil electrode. In this example, pre-formed, biased shape 230 includes a modified S-shaped configuration 246 to hold the lead within the pulmonary artery or a branch of the pulmonary artery.

In some embodiments, any of the pre-formed biased designs discussed above can also be used on lead 100 having the pre-formed, biased J-shape 120 (FIG. 1).

Figure 6:
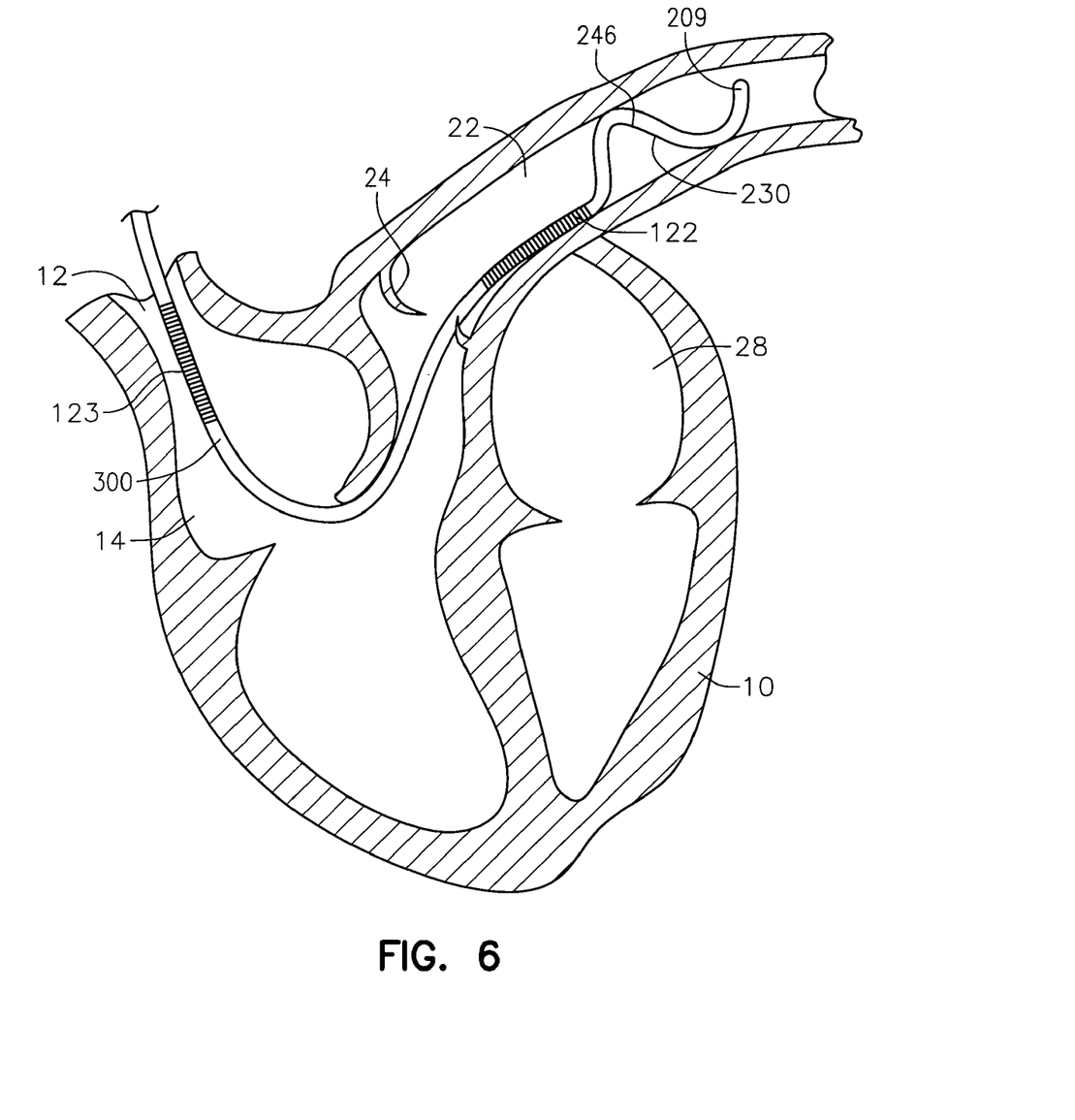
FIG. 6 shows a view of the lead of FIG. 5, implanted within a heart.

FIG. 6 shows lead 300 implanted within heart 10 such that electrode 123 is within the superior vena cava 12 or right atrium 14, and electrode 122 is within pulmonary artery 22, past valve 24. In use, a therapy system utilizing lead 300 can deliver shocks for left atrial defibrillation, right atrial defibrillation, biatrial defibrillation, or be used as a triad system using the pulse generator case as an electrode. In some embodiments, lead 300 can include a pre-formed J-shape such as shape 120 (FIG. 1) discussed above.

In one example use of one or more of the leads discussed herein, the lead is inserted through the right ventricle and into the pulmonary artery using a guiding catheter or a stylet. The lead is positioned until the distal end of the lead is within the pulmonary artery and a shock electrode is located past the pulmonary valve. In one embodiment, the lead can be held in place by either the pre-formed J-shape or the passive fixation techniques discussed above. The lead is coupled to a pulse generator, and when the pulse generator detects a need for therapy, the shock pulse is delivered via electrode 122 in either a bipolar or unipolar system. For example, the pulse generator can deliver energy pulses of approximately 0.1 to 50 Joules via the electrode to the left atrium. In some embodiments, a second electrode can be provided for location within the right atrium or superior vena cava, as discussed above.

Figure 7:
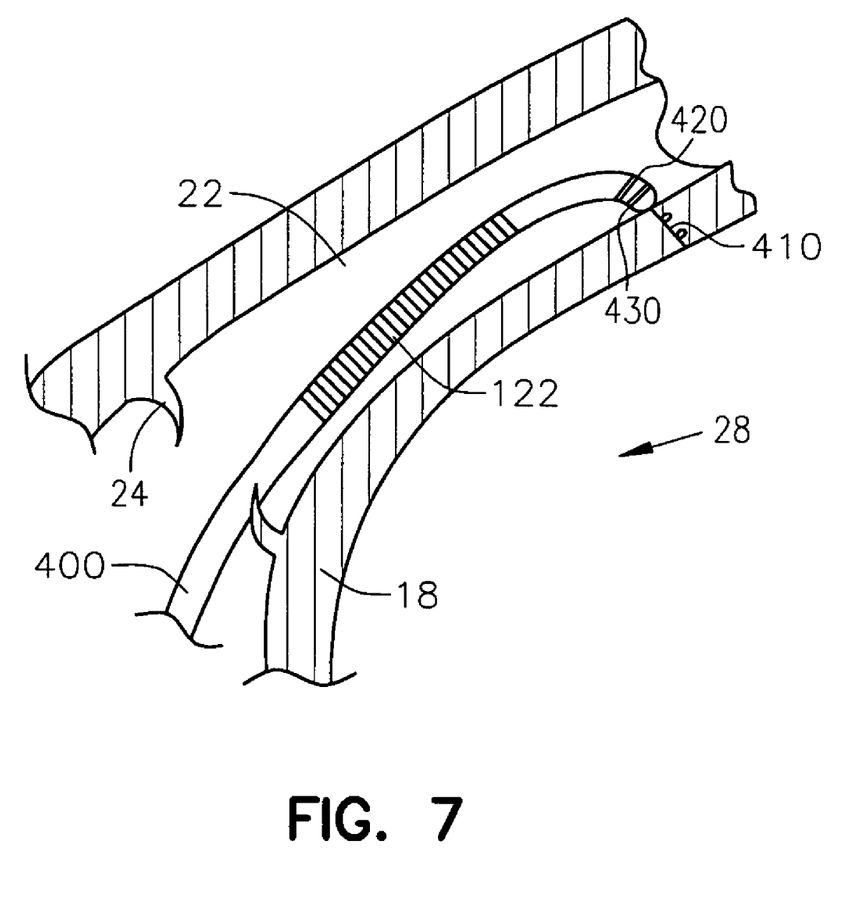
FIG. 7 shows a view of a lead, according to one embodiment, implanted within a heart.

FIG. 7 shows a view of a lead 400 according to one embodiment, implanted within a heart. Lead 400 can include one or more of the components discussed above for leads 100 and 200 and 300 and the above discussions are incorporated herein. In one embodiment, lead 400 is adapted to be actively fixated within the pulmonary artery 22 utilizing a helix 410, or other fixation mechanism, for example. Lead 400 includes electrode 122 which is positionable to apply energy pulses to left atrium 28. In one embodiment, lead 400 includes radiopaque markers 420 near the distal tip to help a physician guide the lead when viewed under fluoroscopy. One embodiment includes a drug elution member 430, which can elute steroids, for example, to reduce inflammatory response of the tissue. In some embodiments, active fixation can be provided in addition to or in place of the passive fixation design discussed above.

Figure 8:
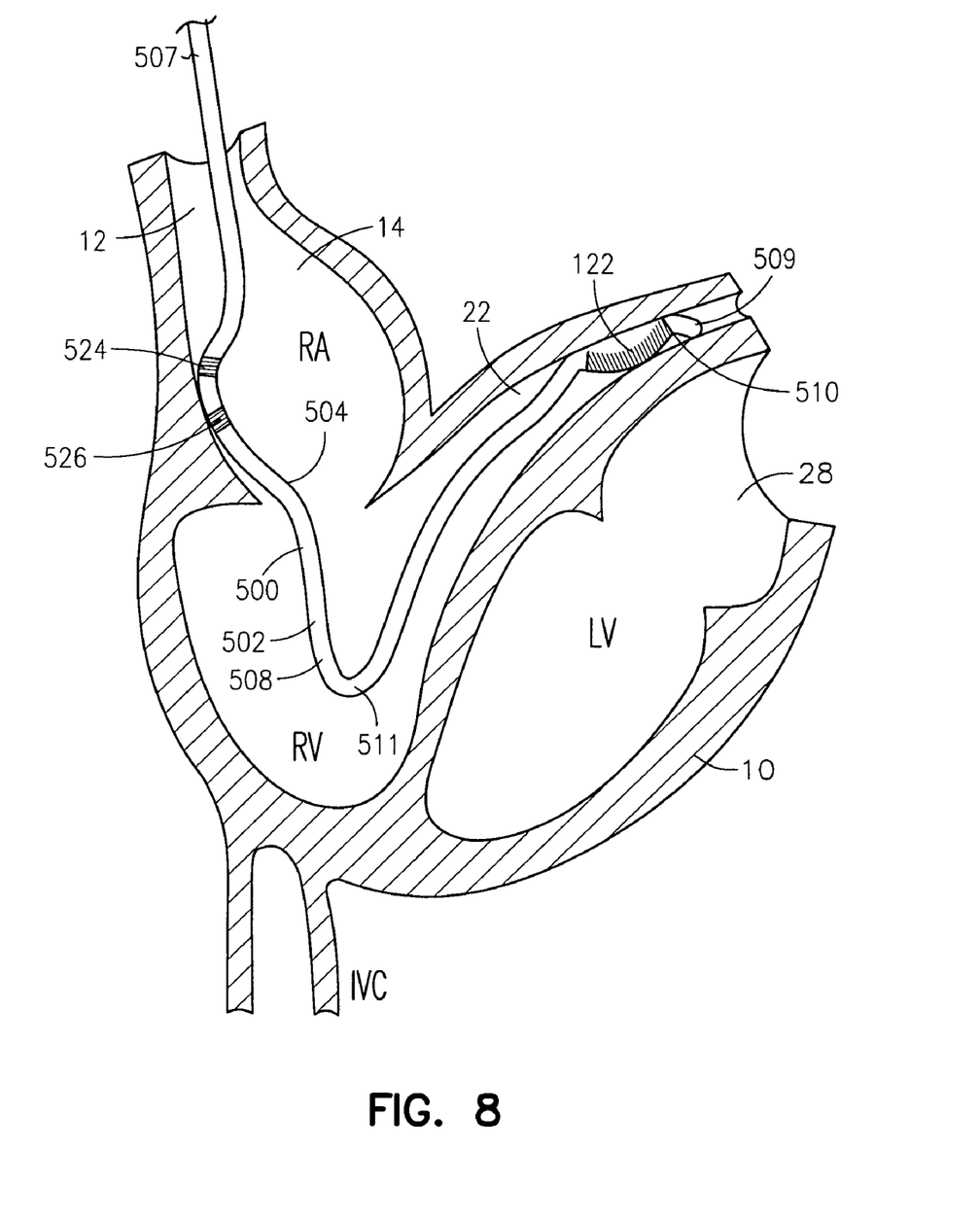
FIG. 8 shows a view of a lead, according to one embodiment, implanted within a heart.
Figure 9:
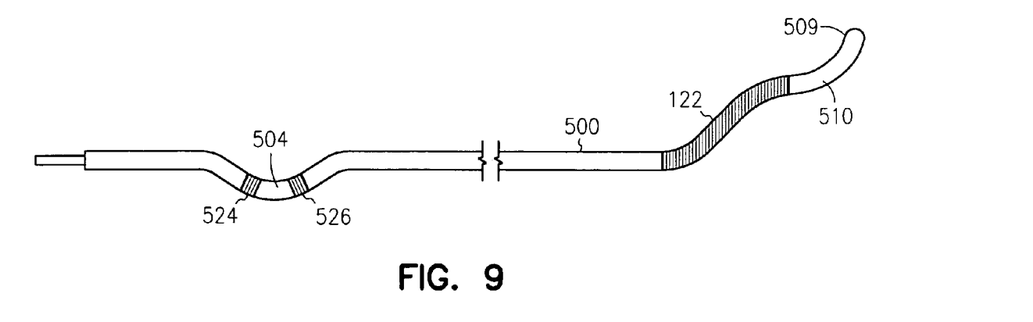
FIG. 9 shows a side view of the lead of FIG. 8.

FIGS. 8 and 9 show a view of a lead 500 according to one embodiment. In FIG. 8, lead 500 is implanted within heart 10. Lead 500 is a single-pass lead adapted to be passively or actively fixated within pulmonary artery 22 utilizing a fixation mechanism such as a preformed biased shape 510 on distal end 509, or other passive or active fixation technique as discussed above. Lead 500 includes a lead body 502 extending from a proximal end 507 to a distal end 509 and having an intermediate portion 508. Coil electrode 122 is disposed proximate distal end 509 and positionable within pulmonary artery 22 so as to deliver energy pulses to left atrium 28.

Lead body 502 also includes one or more electrodes 524, 526 disposed along the intermediate portion of the lead. Electrodes 524, 526 are adapted for positioning and/or fixation to the wall of right atrium 14 of the heart. For example, in one embodiment lead body 502 also includes a preformed biased portion such as a curved portion 504 which facilitates the positioning and fixing of electrodes 524, 526 to the right atrium. Curved portion 504 is positioned in the right atrium 14 of the heart after implantation, and positions the electrodes 524, 526 closer to the wall of the atrium to enhance the sensing and pacing performance of the lead. In one embodiment, electrodes 524, 526 are adapted for delivering atrial pacing therapy. Electrodes 524, 526 can also be used for atrial sensing.

Electrodes 524, 526 can be ring electrodes which can be exposed or partially masked by the lead body. In some embodiments, the electrodes can be hemispherical tip electrodes. In some embodiments, the electrodes can have a porous surface to help fixation to the atrium. In one embodiment, electrodes 524, 526 can be placed on the outside of the curved portion of the lead body.

Lead 500 is implantable such that electrode 122 is within the pulmonary artery and electrodes 524 and 526 are within right atrium 14. This allows for shocking of the left atrium via electrode 122 as well as pacing/sensing at the right atrium using electrodes 524, 526 of the single-pass lead. The configuration of lead 500 allows for right atrium pacing and sensing along with left atrial shocking via the pulmonary artery using a single lead. In one example, the lead can be used for atrial defibrillation therapy. Moreover, the single-pass lead design with passive fixation of the electrode in the pulmonary artery is easier to implant and explant than a lead implanted through the coronary sinus.

In some embodiments, the lead can include steroid elution proximate to or from any of the electrodes 122, 524, and 526. Drug elution, typically steroid, can be provided by using one or more of the drug-releasing technologies such as sleeves or collars positioned in close proximity to the electrodes or by the use of internalized drug-containing plugs. An example of the composition of at least one collar is dexamethasone acetate in a simple silicone medical adhesive rubber binder or a steroid-releasing plug similarly fabricated.

In one embodiment, lead body 502 can include a preformed V-shape or J-shape 511 on the intermediate portion of the lead. J-shape 511 is configured to bias distal end 509 of lead 500 towards pulmonary artery 22 when the lead is implanted within heart 10. Thus, in one embodiment, J-shape 511 helps dispose electrode 122 in the pulmonary artery 22 when the pacing electrodes 524 and 526 are within the right atrium or superior vena cava.

Figure 10:
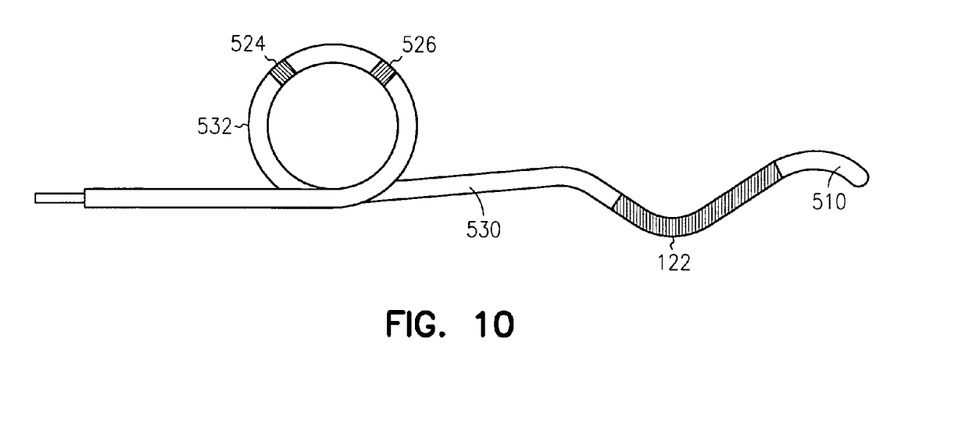
FIG. 10 shows a side view of a lead according to one embodiment.

FIG. 10 shows a lead 530 according to one embodiment. Lead 530 can includes similar features as lead 500 (FIGS. 8 and 9), and the above discussion is incorporated herein. Lead 530 includes shocking coil electrode 122 on a distal end of the lead, with the distal end including a preformed biased section 510, which is adapted to passively fixate the distal portion of the lead within a pulmonary artery. Lead 530 also includes pacing/sensing electrodes 524, 526 on an intermediate portion of the lead. A preformed biased section 532 is located on the intermediate portion of the lead at the location of electrodes 524 and 526. In one embodiment, biased portion 532 includes a spiral shape with electrode 524 and 526 located along the spiral shaped portion. Biased portion 532 of lead 530 positions the atrial electrodes 524, 526 closer to the wall of the heart in the right atrium 14. This enhances electrical performance as the electrodes will be closer to the portion of the heart where the signal will pass.

Figure 11:
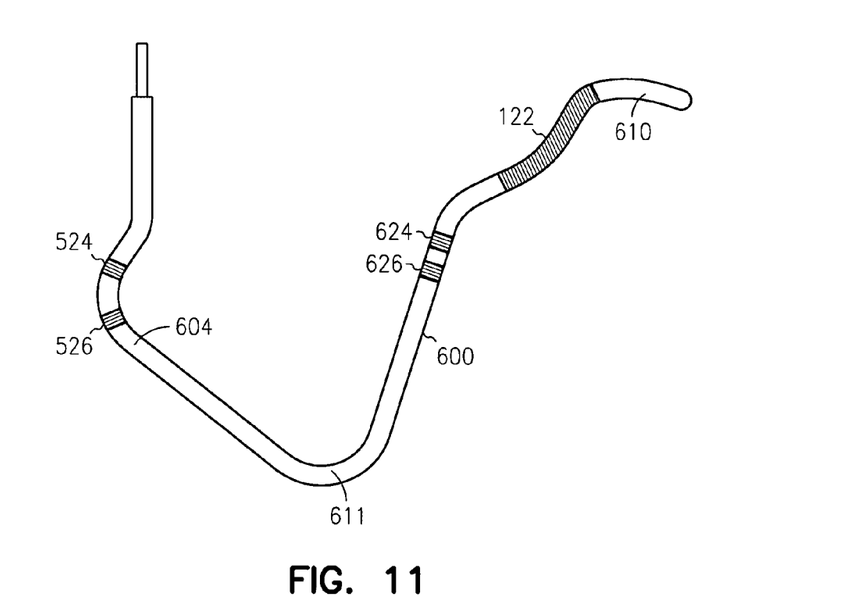
FIG. 11 shows a side view of a lead according to one embodiment.

FIG. 11 shows a lead 600 in accordance with one embodiment. Lead 600 can include features of any of the leads discussed above and the above discussions are incorporated herein by reference. Lead 600 generally includes electrode 122 on a distal section of the lead. The distal section can include a preformed biased section 610, such as discussed above. Lead 600 can also include right atrial electrodes 524 and 526 located on a biased section 604 on an intermediate section of the lead. A pre-formed V-shape or J-shape 611 can be located along an intermediate section of the lead body, such as discussed above.

In one embodiment, lead 600 includes electrodes 624, 626 which are located so as to be proximate to or abut the septum 18 or be within the outflow tract 20 (FIG. 1) when the lead is implanted. For example, lead 600 can be implanted as discussed above such that electrodes 624, 626 are located at the outflow tract or adjacent the RV septum. Electrodes 524, 526 are then located in the right atrium or superior vena cava and electrode 122 is within the pulmonary artery.

Such an embodiment allows for right ventricle septal pacing/sensing, while it further allows for left atrium shocking via electrode 122 and right atrium pacing/sensing using electrodes 524, 526 of the single-pass lead 600. Moreover, electrodes 624, 626 can provide pacing/sensing without being actively fixated to the septum. This reduces the complications resulting from active fixation, such as trauma to the endocardium tissue and higher pacing thresholds. Moreover, the location of electrodes 624, 626 at proximate the septum or outflow tract provides an alternative to right ventricle apex fixation.

Figure 12:
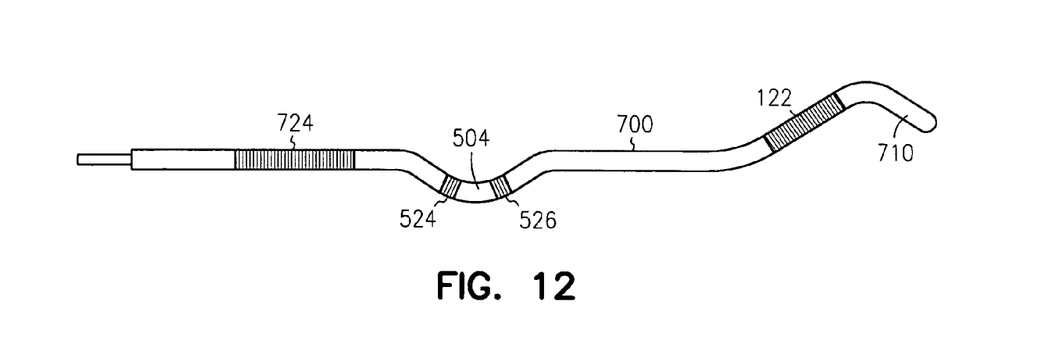
FIG. 12 shows a side view of a lead according to one embodiment.

FIG. 12 shows a lead 700 according to one embodiment. Lead 700 can include features of any of the leads discussed above. Generally, lead 700 includes electrode 122 on a preformed biased distal portion 710 of lead 700. Lead 700 can also include electrodes 524 and 526 on a preformed biased intermediate section 504. In one embodiment, lead 700 includes a second shocking electrode, such as electrode 724, disposed along an intermediate portion of the lead. Electrode 724 is located proximally from electrodes 524, 526 and is configured to be located within the superior vena cava or right atrium when the lead is implanted. For example, lead 700 can be implanted such that distal portion 710 is passively fixated within the pulmonary artery and distal electrode 122 is within the pulmonary artery, electrodes 524 and 526 are within the right atrium, and coil electrode 724 is within the superior vena cava. Such as design provides for a-triad therapy using a single lead, for example.

In various embodiments, the spacing of electrodes 122 and 724 can be varied to account for anatomical differences. Moreover, in some embodiments, any of the leads discussed above can include a proximal electrode, such as electrode 724, for providing shock therapy at the right atrium or superior vena cava.

In one example, leads such as discussed above can be implanted by inserting the lead body through a right ventricle and into a pulmonary artery and fixating the shocking electrode within the pulmonary artery and disposing a pacing electrode within a right atrium or superior vena cava. The leads can be inserted using catheters, stylets or guidewires. The distal end of the lead can include a pre-formed, biased shape adapted to passively fixate the distal end of the lead body within a pulmonary artery. The shocking electrode can deliver shocking pulses to the left atrium having an energy ranging from approximately 0.1 Joules to approximately 50 Joules to deliver atrial defibrillation therapy. The pacing electrodes can provide pacing/sensing within the right atrium or superior vena cava. In some examples, a preformed, biased shape, such as a curve or spiral, can be formed on the lead proximate the location of the pacing electrodes to help bias the electrodes towards the right atrial wall. Further embodiments provide a second shocking electrode to deliver shocking pulses with the superior vena cava or a right atrium.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead comprising:
  a lead body extending from a proximal end to a distal end and having an intermediate portion;
  a shocking electrode disposed proximate the distal end of the lead body; and
  a pacing electrode disposed along the intermediate portion of the lead body;
  wherein the distal end of the lead body includes a pre-formed biased shape, and wherein the lead body is shaped to be placed within a heart with the lead body extending through the right ventricle and the pre-formed biased shape positioned within a pulmonary artery, and wherein the lead body is configured into a pre-formed J-shape with the shocking electrode located distally from a bottom of the J-shape and the pacing electrode located proximally from the bottom of the J-shape; and
  wherein the lead body includes a second preformed, biased shape near the location of the pacing electrode, the second preformed, biased shape including a spiral shape.

2. The lead of claim 1, wherein the lead body is shaped to be positioned within a heart such that a shock can be delivered to the left atrium via the shocking electrode.

3. A lead comprising:
  a lead body extending from a proximal end to a distal end and having an intermediate portion;
  a shocking electrode disposed proximate the distal end of the lead body; and
  a pacing electrode disposed along the intermediate portion of the lead body, wherein the distal end of the lead body includes a pre-formed biased shape wherein the pacing electrode is located along the intermediate portion of the lead body in a position such that the pacing electrode is located within a right atrium or superior vena cava when the shocking electrode is within a pulmonary artery, and wherein the lead body includes a second preformed, biased shape near the location of the pacing electrode, wherein the second preformed, biased shape includes a spiral shape.

4. The lead of claim 3, wherein the lead body includes a second shocking electrode disposed along the lead proximally from the pacing electrode.

5. The lead of claim 3, further comprising a second pacing electrode disposed on the intermediate portion of the lead and located on the lead so as to be located proximate a ventricular outflow tract when the distal portion of the lead is within the pulmonary artery.

6. The lead of claim 5, wherein the lead body is configured into a pre-formed J-shape with the shocking electrode located distally from a bottom of the J-shape and the pacing electrode located proximally from the bottom of the J-shape.

7. The lead of claim 3, wherein the second preformed, biased shape is adapted to bias the pacing electrode toward a wall of the right atrium or the superior vena cava.

8. The lead of claim 3, wherein the pre-formed, biased shape on the distal end of the lead includes an S-shaped configuration.

9. The lead of claim 3, wherein the pre-formed, biased shape on the distal end of the lead includes a spiral configuration.

10. The lead of claim 3, wherein the pre-formed, biased shape on the distal end of the lead includes at least two surfaces positioned to contact opposing walls of the pulmonary artery.

11. The lead of claim 3, wherein the lead body includes a pre-formed J-shape along the intermediate section of the lead body.

12. The lead of claim 3, wherein the lead body includes a pre-formed J-shape along the intermediate section of the lead body.

13. A lead comprising:
  a lead body extending from a proximal end to a distal end and having an intermediate portion, the distal end including pulmonary artery passive fixation features;
  a shocking electrode disposed along the distal end of the lead body; and
  a pacing electrode disposed along the intermediate portion of the lead body, wherein the lead body includes a pre-formed, biased shape near the location of the pacing electrode, wherein the preformed, biased shape includes a spiral shape; and
  wherein the lead body is configured such that when the shocking electrode is within a pulmonary artery the pacing electrode is located within a right atrium or a superior vena cava.

14. The lead of claim 13, wherein the lead body includes a second shocking electrode disposed along the lead and located proximally from the pacing electrode.

15. The lead of claim 13, further comprising a second pacing electrode disposed on the intermediate portion of the lead and located on the lead so as to be located proximate a ventricular outflow tract when the distal portion of the lead is within the pulmonary artery.

16. The lead of claim 15, wherein the lead body is configured into a pre-formed J-shape with the shocking electrode located distally from a bottom of the J-shape and the pacing electrode located proximally from the bottom of the J-shape.

17. A method comprising:
providing a lead having a lead body extending from a proximal end to a distal end and having an intermediate portion, the lead body having a shocking electrode disposed proximate the distal end and a pacing electrode disposed along an the intermediate portion, wherein the lead body includes a preformed, biased shape near the location of the pacing electrode, the preformed, biased shape including a spiral shape;
inserting the lead body through a right ventricle and into a pulmonary artery and passively fixating the shocking electrode within the pulmonary artery and disposing the pacing electrode within a right atrium or superior vena cava, and
disposing a second pacing electrode proximate a ventricular outflow tract when the distal portion of the lead is within the pulmonary artery.

18. The method of claim 17, further comprising;
delivering pulses from the shocking electrode to a left atrium.

19. The method of claim 18, wherein the pulses have an energy ranging from approximately 0.1 Joules to approximately 50 Joules.

20. The method of claim 17, wherein providing a lead includes providing a lead body wherein the distal end of the lead body includes a second pre-formed, biased shape adapted to passively fixate the distal end of the lead body within the pulmonary artery.

21. The method of claim 17, further comprising providing a second shocking electrode disposed along the lead body and disposed within a superior vena cava or a right atrium.

22. The method of claim 17, further comprising providing a preformed biased shape along the intermediate portion of the lead near the pacing electrode wherein the preformed biased shape biases the pacing electrode toward a wall of the right atrium or the superior vena cava.

23. The method of claim 17, further comprising providing a pre-formed J-shape in the intermediate portion of the lead with the shocking electrode located distally from a bottom of the J-shape and the pacing electrode located proximally from the bottom of the J-shape.

* * * * *

UNITED STATES PATENT AND TRADEMARK OFFICE
CERTIFICATE OF CORRECTION

PATENT NO. : 7,555,351 B2  Page 1 of 1
APPLICATION NO. : 10/895748
DATED : June 30, 2009
INVENTOR(S) : Yongxing Zhang et al.

It is certified that error appears in the above-identified patent and that said Letters Patent is hereby corrected as shown below:

In column 9, line 10, in Claim 17, delete "an the" and insert -- the --, therefor.

In column 9, line 22, in Claim 18, delete "comprising;" and insert -- comprising --, therefor.

Signed and Sealed this

Sixth Day of October, 2009

David J. Kappos
*Director of the United States Patent and Trademark Office*